United States Patent
Vitzthum et al.

(10) Patent No.: US 12,203,831 B2
(45) Date of Patent: Jan. 21, 2025

(54) COMPOSITIONS AND METHODS FOR REMOVING INTERFERING SUBSTANCES

(71) Applicant: Siemens Healthcare Diagnostics Inc., Tarrytown, NY (US)

(72) Inventors: Frank Vitzthum, Biedenkopf (DE); Huey Lee, Millwood, NY (US); Michelle Son, Hopewell Junction, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 584 days.

(21) Appl. No.: 17/250,853

(22) PCT Filed: Sep. 23, 2019

(86) PCT No.: PCT/US2019/052341
§ 371 (c)(1),
(2) Date: Mar. 12, 2021

(87) PCT Pub. No.: WO2020/068609
PCT Pub. Date: Apr. 2, 2020

(65) Prior Publication Data
US 2022/0042886 A1   Feb. 10, 2022

Related U.S. Application Data

(60) Provisional application No. 62/738,925, filed on Sep. 28, 2018.

(51) Int. Cl.
*A61K 9/127* (2006.01)
*G01N 1/34* (2006.01)
*G01N 1/40* (2006.01)

(52) U.S. Cl.
CPC ............... *G01N 1/34* (2013.01); *G01N 1/405* (2013.01); *A61K 9/127* (2013.01)

(58) Field of Classification Search
CPC ...................................................... A61K 9/127
See application file for complete search history.

(56) References Cited

U.S. PATENT DOCUMENTS

| 5,212,063 | A | 5/1993 | Ofenloch-Hahnle et al. |
| 7,125,707 | B2 | 10/2006 | Sleytr et al. |
| 2005/0266512 | A1* | 12/2005 | Buckley ............ C12Q 1/37 435/23 |
| 2011/0097392 | A1* | 4/2011 | Wang ............ A61P 25/00 435/375 |
| 2012/0039990 | A1 | 2/2012 | Reshetnyak et al. |

(Continued)

FOREIGN PATENT DOCUMENTS

JP   S62104844   5/1987

OTHER PUBLICATIONS

Lemiere, Joel et al: "(alpha)—Hemplysin membrane pore density measured on liposomes"; Soft Matter (Print); vol. 9, No. 11, Jan. 1, 2013.

(Continued)

*Primary Examiner* — Benjamin J Packard (57) ABSTRACT

Disclosed herein are compositions and methods for removing interfering substances from biological samples, biochemical assays, or reagents used in biological samples using porous liposomes that capture and in some instances enrich said interfering substances within the liposomes.

37 Claims, 4 Drawing Sheets

(56) References Cited

U.S. PATENT DOCUMENTS

2017/0173177 A1    6/2017   Bangera et al.
2017/0190798 A1    7/2017   Jing

OTHER PUBLICATIONS

Majd S. et al: "Applications of biological pores in nanomedicine, sensing and nanoelectronics"; Current Opinion in Biotechnology, London, GB, vol. 21, No. 4, Aug. 1, 2010.
International Search Report for PCT/US2019/052341 dated Nov. 22, 2019.

* cited by examiner

COMPOSITIONS AND METHODS FOR REMOVING INTERFERING SUBSTANCES

TECHNICAL FIELD

Disclosed herein are compositions and methods for removing interfering substances from, for example, biological samples using porous liposomes.

BACKGROUND

Biochemical assays, such as immunoassays, clinical chemistry assays, and other medical and/or diagnostic tests, are important tools that allow researchers and clinicians to test samples for the presence or absence of substances or biomolecules. Biochemical assays typically capitalize on affinity of ligands or substrates for specific biomolecules, for example antibodies, recombinant antibodies, antibody fragments, Affimers®, affibodies, DNA-aptamers, RNA-aptamers, enzymes, etc. The specific interaction between ligands and their target biomolecules that bind them allows biochemical assays to detect, isolate, and quantify the target biomolecule (or "analyte") in, for example, a biological sample from a subject.

However, the presence in biochemical assays of interfering substances (or "interferents"), including, for example, biotin, fluorescein, and bilirubin, can interfere with the specific interaction between the ligand(s) and the target biomolecule, and in some cases can inhibit or reduce interaction and thereby impact the detection in the biochemical assay. In some cases, interfering substances can lead to false associations between ligand(s) and target molecules. This interference in biochemical assays can cause erroneously high or erroneously low detection of biomolecules, or false positive or false negative results, depending on the ligand (s)/probes used and the experimental design of the assay. In this way, interfering substances in biochemical assays can lead to inaccurate diagnosis and misguided treatment decisions.

Present methods for detecting interfering substances in biochemical assays include conducting separate tests on biological samples before and/or after performing the biochemical assay. This requires additional time and resources. When such separate testing identifies an interfering substance in a biological sample before a biochemical assay is performed, the assay must be tailored to accommodate the interfering substance, or the assay result must be flagged and assessed for reliability in view of the presence of interfering substance. In some cases, the "Instruction for Use" or IFU of a particular assay will include guidance for assessing how and when assay results can be relied upon, if interfering substances are detected or suspected. All of these measures require additional time and resources. In addition to separate testing, patient anamnesis or patient education or both can prevent or reduce the problem of interfering substances in biochemical assays. For example, in assays involving the interference of biotin, patient anamnesis can inform the physician that biotin levels are excessively high due to intake of biotin as a medication or nutritional supplement. Through patient education, patients may refrain from taking interfering substances like biotin before a biochemical assay is performed. Reliance on patient anamnesis and education, however, are fraught with problems of inconsistent or inaccurate patient reporting and patient non-compliance.

Other compositions and methods for addressing the problem of interferents in biochemical assays have been put forth. U.S. Pat. No. 5,212,063 purports to describe compositions to reduce and prevent interferents whereby free biotin is removed "by incubating the sample solution with polymer particles consisting of a [polymer] core and a covering [wherein the polymer core] has a plurality of binding sites for biotin and [the covering has] at least one layer of protein, peptide, carbohydrate or co-polymer of carbohydrate and amino acids." However, such polymer particles present challenges, including, for example, tendency of the particles to precipitate or aggregate in solution, and limited surface area useful for capturing interferents in a solution. A need exists for compositions and methods for reducing the effect of interfering substances on biochemical assays, including, for example, immunoassays and clinical chemistry assays, among other clinical/medical diagnostic tests. Compositions and methods for removing, sequestering, and separating interfering substances from biochemical assays are also needed.

SUMMARY

It is an object of the present patent application to provide compositions and methods for removing interfering substances from biological samples and to provide compositions and methods for removing interfering substances from reagents used in biochemical assays. Preferred compositions and methods include porous liposomes that capture interfering substances present in a fluid for use in a biochemical assay. The described porous liposomes' capacity to capture interferents is not limited to surface area of a particle; rather, their capacity to capture interferents includes the entire interior volume of the liposomes. Further, the molecular compositions of the described porous liposomes can allow them to achieve neutral buoyancy within a given solution, thereby avoiding precipitation and/or aggregation.

Described herein are compositions comprising an artificially formed liposome comprising an interior, a lipid bilayer, and a pore-forming substance in the lipid bilayer. In a preferred embodiment, a binder is disposed in the liposome. The pore-forming substance forms pores in the lipid bilayer. The pore-forming substance can comprise a pore-forming protein or protein complex. In some cases, the pore-forming substance comprises porin, hemolysin, nucleoporin, membrane attack complex (MAC), complement component C9, or subunits, combinations, or multimers of porin, hemolysin, nucleoporin, membrane attack complex (MAC), and complement component C9. The compositions can comprise about 1 µg/ml to about 100 µg/ml of the pore-forming substance expressed in terms of µg of protein per ml of 100 µM liposome containing solution. The compositions preferably comprise about 20 µg/ml of the pore-forming substance expressed in terms of µg of protein per ml of 100 µM liposome containing solution.

In some embodiments of the compositions described herein, the pores allow passage of one or more interferents into the liposome. The pores can have an inner diameter of about 0.5 nanometers to about 12 nanometers. Alternatively or additionally, the pores can have an exclusion limit of about 250 to about 5000 Da.

In some embodiments, a binder is disposed in the liposome. The binder can preferentially have a maximum cross-section that is greater than the inner diameter of the pores. Alternatively or additionally, the binder can have a molecular weight greater than the exclusion limit of the pores. The binder can comprise one or more binding sites, each binding site having an affinity for one or more interferents. In some embodiments, the binder comprises avidin, streptavidin, or neutravidin. At least a portion of the binder can be disposed in the lipid bilayer, with the binding sites directed toward the interior of the liposome—that is, with the binding sites of the binder exposed to the interior volume of the liposome. Alternatively, the binder can be disposed entirely within the interior of the liposome. In some embodiments, the binder is an antibody, an aptamer, an affibody, an affimer, or a fragment of an antibody, an aptamer, an affibody, or an affimer. The affinity of the binding site of the binder for the one or more interferents can be an immunospecific affinity. In some embodiments, the one or more interferents can be a component of or a part of the architecture or set up of the biochemical assay, as described in detail herein.

In some embodiments, the liposome is permeable to substances having a molecular weight of less than about 600 Da, and impermeable to substances having a molecular weight of about 600 Da or greater.

In some embodiments, the liposome is about 100 nanometers to about 1000 nanometers in diameter. In some embodiments, the liposome can be about 200 nanometers in diameter.

In some embodiments, the lipid bilayer can comprise high melting point phospholipids with sterols.

The composition can be a suspension. The suspension can comprise a buffer. The suspension can have a pH-value of about 7.4. The composition can be reconstituted from a lyophilized composition. The composition itself can be lyophilized in some embodiments.

Also described herein are methods of preparing a biological sample for analysis comprising incubating the biological sample with the compositions as described herein. The analysis can be an immunoassay, a clinical chemistry assay, or other clinical test, including clinical or medical diagnostic tests. The biological sample can be, for example, whole blood, serum, plasma, urine, saliva, semen, or cerebrospinal fluid. The biological sample can be from a subject including, for example, a mammal. Thus, the methods described herein are applicable to biological samples from human and non-human subjects. The methods described herein are particularly applicable to biological samples from humans.

In some embodiments of the methods described herein, incubating the biological sample with the composition captures within the liposomes one or more interferents from the biological sample. The one or more interferents each can have a maximum cross-section that is less than the inner diameter of the pores or are each less than about 5000 Da. The one or more interferents can comprise, for example, biotin, fluorescein, bilirubin, or combinations thereof. The one or more interferents can be unconjugated. In some embodiments, the one or more interferents have a molecular weight of less than about 600 Da.

Some embodiments of the methods further comprise isolating the liposomes. Isolating the liposomes can comprise using centrifugation, dialysis, filtration, chromatography, magnetic separation, hollow fiber dialysis, or combinations thereof. The methods can further comprise separating or extracting the liposomes from the biological sample.

Also described herein are methods of reducing or eliminating one or more interferents in an assay of a biological sample comprising incubating the biological sample with the compositions described herein.

Also described are methods of making the compositions described in the application.

The application also describes kits comprising the compositions described herein, along with one or more reagents for performing a biochemical assay on a biological sample and instructions for performing the biochemical assay. The instructions can further direct a user to incubate the biological sample with the compositions described herein. In some embodiments, the kits comprise the described lyophilized compositions along with one or more reagents for performing a biochemical assay on a biological sample and instructions for performing the biochemical assay. The instructions can further direct a user to reconstitute the lyophilized composition and incubate the biological sample with the reconstituted composition.

BRIEF DESCRIPTION OF THE DRAWINGS

The summary, as well as the following detailed description, is further understood when read in conjunction with the appended drawings. For the purpose of illustrating the disclosed compositions, methods, and kits, there are shown in the drawings exemplary embodiments; however, the compositions, methods, and kits are not limited to the specific embodiments shown. In the drawings:

FIG. 2A-FIG. 2C show exemplary depictions of biochemical assays with and without interfering substances and/or porous liposomes.

DETAILED DESCRIPTION OF ILLUSTRATIVE EMBODIMENTS

The compositions, methods, and kits described in this patent application may be understood more readily by reference to the following detailed description taken in connection with the accompanying figures, which form a part of the application. It is to be understood that the disclosed compositions, methods, and kits are not limited to the specific embodiments described or shown herein, and that the terminology used herein is for the purpose of describing particular embodiments by way of example only and is not intended to be limiting of the claimed compositions, methods, and kits.

Unless specifically stated otherwise, any description as to a possible mechanism or mode of action or reason for improvement is meant to be illustrative only, and the disclosed compositions, methods, and kits are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges were explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed compositions, methods, and kits which are, for clarity, described herein in the context of separate embodiments, may also be provided in combination in a single embodiment. Conversely, various features of the disclosed compositions, methods, and kits that are, for brevity, described in the context of a single embodiment, may also be provided separately or in any subcombination.

As used herein, the singular forms "a," "an," and "the" include the plural.

Various terms relating to aspects of the patent application are used throughout the application and claims. Such terms are to be given their ordinary meaning in the art unless otherwise indicated. Other specifically defined terms are to be construed in a manner consistent with the definitions provided herein.

The term "comprising" is intended to include examples encompassed by the terms "consisting essentially of" and "consisting of"; similarly, the term "consisting essentially of" is intended to include examples encompassed by the term "consisting of."

The term "liposome" as used herein refers to an artificially formed vesicle or sac made up of a membrane comprising at least one lipid bilayer. The term is understood to exclude naturally occurring vesicles or other naturally occurring membranous substances isolated from cells or biological samples comprising cells. The terms "vesicle" and "liposome" can be synonymous as used herein in reference to the artificially formed sacs comprising a membrane of at least one lipid bilayer. For example, an artificially formed large unilamellar liposome vesicle, or "LUV," is termed a vesicle, but is also referred to as a liposome for purposes of this patent application.

The term "interferent" or "interfering substance" as used herein refers to a substance or substances that are present in and interfere with, for example, a biochemical assay. Interferents can be present in a biological sample, and thereby introduced into a biochemical assay upon mixing of the biological sample with an assay component. Interferents can be present in any assay component in addition to the biological sample. For example, interferents can be present one or more reagent designated for use in a biochemical assay. Examples of interferents include, but are not limited to, biotin, bilirubin, and fluorescein.

As used herein, the mass unit "Dalton" or "Da" refers to molar mass and, for purposes of this application, is equivalent to grams per mole; i.e., 1 Da=1 g/mol.

Described herein are compositions comprising an artificially formed liposome comprising an interior, a lipid bilayer, and a pore-forming substance in the lipid bilayer. In a preferred embodiment a binder is disposed within the liposome. The pore-forming substance typically will have an amphipathic region having a lipophilic or hydrophobic portion that preferentially interacts with the lipid bilayer and a hydrophilic portion that preferentially interacts with the aqueous environment within or surrounding the lipid bilayer. In this way, the pore-forming substance resides within the lipid bilayer of the liposomes described herein, and association of pore-forming substances within the lipid bilayer can assemble pores. Thus, the pore-forming substance can form pores in the lipid bilayer. Such pore formation can arise from the assembly of multiple subunits of the pore-forming substance in the lipid bilayer. The pore-forming substance can comprise a pore-forming protein or protein complex. Examples of pore-forming proteins that can be used as pore-forming substances in the liposomes of the present application include, but are not limited to, monomers, multimers, or combinations monomers and multimers of porin, hemolysin, and nucleoporin. In addition, protein complexes including, for example, the membrane attack complex (MAC) of the complement system, component C9 of the complement system, or subunits, combinations, or multimers of MAC or component C9 can be used as pore-forming substances. The pore-forming substances can be recombinant pore-forming proteins, chimeric pore-forming proteins, genetically engineered pore-forming proteins, or pore-forming proteins conjugated to other molecules of interest. Other molecules of interest, in this sense, can include, for example, epitopes, antigens, or other binding molecules useful for labelling and/or purifying the pore-forming substances or liposomes comprising them. The other molecules of interest can also or alternatively be useful for isolating the pore-forming substances or liposomes comprising them. For example, in some embodiments, the pore-forming substance can be conjugated to a 6-his tag (6-histidine), a Myc tag, an HA tag, FLAG tag, or similar epitope tag to facilitate isolation of the liposomes from a mixture comprising the compositions described herein and, for example, a biological sample.

The liposomal compositions can comprise about 1 µg/ml to about 100 µg/ml of the pore-forming substance expressed in terms of µg of protein per ml of 100 µM liposome containing solution. The pore-forming substance is present at about 1 µg/ml to about 10 µg/ml, about 10 µg/ml to about 20 µg/ml, about 20 µg/ml to about 30 µg/ml, about 30 µg/ml to about 40 µg/ml, about 40 µg/ml to about 50 µg/ml, about 50 µg/ml to about 60 µg/ml, about 60 µg/ml to about 70 µg/ml, about 70 µg/ml to about 80 µg/ml, about 80 µg/ml to about 90 µg/ml, or about 90 µg/ml to about 100 µg/ml expressed in terms of µg of protein per ml of 100 µM liposome containing solution. The compositions preferably comprise about 20 µg/ml of the pore-forming substance expressed in terms of µg of protein per ml of 100 µM liposome containing solution.

In some embodiments of the compositions described herein, the pores allow passage of one or more interferents into the liposome. The one or more interferents can pass through the pores in the lipid bilayer via diffusion, including, for example, passive diffusion. The pores can have an inner diameter that varies depending on the pore-forming substance used. For example, in some embodiments the pores can have an inner diameter of about 0.5 nanometers to about 12 nanometers. The pores can have an inner diameter of from about 0.5 nanometers to about 1.5 nanometers, about 1.5 nanometers to about 2.5 nanometers, about 2.5 nanometers to about 3.5 nanometers, about 3.5 nanometers to about 4.5 nanometers, about 4.5 nanometers to about 5.5 nanometers, about 5.5 nanometers to about 6.5 nanometers, about 6.5 nanometers to about 7.5 nanometers, about 7.5 nanometers to about 8.5 nanometers, about 8.5 nanometers to about 9.5 nanometers, about 9.5 nanometers to about 10.5 nanometers, about 10.5 nanometers to about 11.5 nanometers, or about 12 nanometers. Pores having an inner diameter of about 4 nm, for example, can be achieved using the pore-forming protein P13 from *B. burgdorferi* porin. Pores having an inner diameter of about 5 nm, for example, can be achieved using the pore-forming protein complex C5b-9 of the complement system. Pores having an inner diameter of about 10 nm, for example, can be achieved using the pore-forming protein tubular poly-C9 without C5b-8. Thus, depending on the pore-forming protein(s) selected for use in the liposomal compositions, including the species or variants from which the pore-forming protein is derived and the combination of subunits or multimers, the inner diameter of the pores can be manipulated across a range of diameters. (See, for example: Tegla, Cosmin A., et al. "Membrane attack by complement: the assembly and biology of terminal complement complexes." *Immunologic research* 51.1 (2011): 45; Welte, Wolfram, et al. "Structure and function of the porin channel." *Kidney international* 48.4 (1995): 930-940; and Dudkina, Natalya V., et al. "Structure of the poly-C9 component of the complement membrane attack complex." *Nature communications* 7 (2016): 10588; the disclosures of each of which are hereby incorporated by reference in their entirety.) In this way, the pore size of the porous liposomes can be optimized to allow selective permeability of interferents of particular size.

Another way to classify pore size or liposome porosity is to consider the exclusion limit or molecular mass cut-off of the pores formed by the pore-forming substance. The terms "exclusion limit" and "molecular mass cut-off" are used interchangeably in this application to describe the maximum molecular weight of a molecule or substance that can pass through a pore. For example, certain pore-forming proteins, when introduced into a lipid bilayer, form pores that allow particles to diffuse through the pore and thereby traverse the lipid bilayer only if the particles are below the size exclusion limit or the molecular mass cut-off of the pore created by the pore-forming proteins. For example, porins typically have an exclusion limit of from about 600 Da to about 5000 Da, and specific porins, depending on species and variant, have been shown to create pores having exclusion limits across this range. P13 from *B. burgdorferi*, for instance, has a 400 Da molecular mass exclusion limit. In some embodiments, the pores can have an exclusion limit of about 250 to about 5000 Da. The pores can have an exclusion limit of about 250 Da, about 500 Da, about 750 Da, about 1000, Da, about 1250 Da, about 1500 Da, about 1750 Da, about 2000 Da, about 2250 Da, about 2500 Da, about 2750 Da, about 3000 Da, about 3250 Da, about 3500 Da, about 3750 Da, about 4000 Da, about 4250 Da, about 4500 Da, about 4750 Da, or about 5000 Da.

In some embodiments, the porous liposomes described herein have pores formed other than by pore-forming proteins. For example, porous phospholipid nanoshells (“PPNs”) can be employed (see, for example, Cheng, Zhiliang, Gemma D. D’Ambruos, and Craig A. Aspinwall. “Stabilized porous phospholipid nanoshells.” *Langmuir* 22.23 (2006): 9507-9511, the disclosure of which is incorporated herein by reference in its entirety). PPNs such as those disclosed by Cheng et al can have a reactive phospholipid membrane, a cross-linking reagent, and a photoinitiator to polymerize and “shrink” the pores in such a way that small molecules (<2000 Da) can penetrate the phospholipid membrane while encapsulated proteins, for example, remain inside the vesicles.

In some embodiments, the compositions comprise a binder disposed in the liposome, wherein the binder has a maximum cross-section that is greater than the inner diameter of the pores. Alternatively or additionally, the binder can have a molecular weight greater than the exclusion limit or molecular weight cut-off of the pores formed by the pore-forming substance. In this way, the binder can be entrapped within liposome, unable to diffuse through the pores in the lipid bilayer because of the pores’ size exclusion limit. In some embodiments, the binder is about 5000 Da and the pores formed by the pore-forming substance have an exclusion limit less than 5000 Da. At least a portion of the binder can be disposed in the lipid bilayer, with the binding sites directed toward the interior of the liposome—that is, with the binding sites of the binder exposed to the interior volume of the liposome. It is foreseeable that a binder disposed in the lipid bilayer in this manner could have a portion of its binding sites oriented outward toward the exterior of the liposomes, or could have all or a portion of its binding sites oriented outward toward the exterior of the liposomes for a transitory period of time. It is to be appreciated that, even in this arrangement, the orientation of a portion of the binding sites toward the exterior of the liposome rather than toward the interior would have a negligible impact on the assay performance. Alternatively, the binder can be disposed entirely within the interior of the liposome. The binder can be any molecule or substance having binding specificity for one or more interferents. The binder can comprise one or more binding sites, each binding site having an affinity for one or more interferents. The affinity of the binding sites of the binder for the one or more interferents can be an immunospecific affinity. The binding affinity of the binder for the one or more interferents permits the binder to capture the interferents that diffuse into the liposome, and thereby enables the liposome to enrich the interferents inside the liposome. Enrichment, in this context, refers to the capability of a liposome to capture a higher concentration of interferent in the internal environment of the liposome than would be achieved under equilibrium conditions without the binder. In other words, enriching interferents within the liposome in this manner yields a disproportionately high concentration of interferents captured within the liposomes, and thereby removes more interferents from the environment external to the liposomes, i.e., removes interferents from the reaction volume of a biochemical assay reaction mixture.

In some embodiments, the binder comprises avidin or an avidin derivative, including for example streptavidin, or neutravidin. In some embodiments, the binder is an antibody, an aptamer, an affibody, an affimer, or a fragment of an antibody, an aptamer, an affibody, or an affimer. The binder can be a recombinant, chimeric, genetically engineered, or conjugated protein, including, for example, an antibody, aptamer, affibody, affimer, or fragment thereof. In some embodiments, the binder is a recombinant antibody or antibody fragment. The binder can include epitopes, antigens, or other modifications useful for molecularly or immunogenically labelling, expressing, or purifying the binder. For example, in some embodiments, the binder can be conjugated to a 6-his tag (6-histidine), a Myc tag, an HA tag, FLAG tag, or similar epitope tag to facilitate isolation, separation, or extraction of the binder from a reaction mixture comprising the compositions described herein and, for example, a biological sample. The binder, disposed within the liposomes of some embodiments of the described compositions, can be extracted from the liposomes by use of suitable detergents or membrane disrupting mechanical forces. In this way, the binder can be separated from the liposomes after a biochemical assay is conducted in order to determine the amount of interferent associated with the binder.

The one or more interferents as referred to in this patent application can be any molecule or substance that is known to interfere with molecular interactions between components of a biochemical assay. In some embodiments, the one or more interferents each has a maximum cross-section that is less than the diameter of the pores. Alternatively or additionally, the one or more interferents each has a molecular weight less than the exclusion limit of the pores formed by the pore-forming substance. In some embodiments, the molecular weight of the one or more interferents can be less than about 5000 Da, less than about 4000 Da, less than about 3000 Da, less than about 2000 Da, less than about 1000 Da, less than about 900 Da, less than about 800 Da, less than about 700 Da, or less than about 600 Da. Thus, the one or more interferents each can diffuse into the liposomes of the compositions described herein through the pores. The diffusion can be via passive diffusion through the pores. Examples of interferents that can be captured in the liposomes of the described compositions include, for example, biotin, fluorescein, bilirubin, or combinations thereof. In some embodiments, the one or more interferents can be unconjugated. Thus, the methods and compositions described can have improved sensitivity and efficacy by eliminating unconjugated interferents where conjugated counterparts are used as an assay component. An unconjugated interferent is, for example, free biotin, as distinguished from conjugated biotin or biotin-conjugates. When such biotin conjugates are used as ligands, probes, or other components of a biochemical assay, the likelihood increases that any amount of free biotin (unconjugated biotin) present in the biochemical assay will interfere with or inhibit the biotin-conjugate's target interaction and thereby inhibit or reduce the target interaction and the overall efficacy of the biochemical assay. This is avoided by the presently described compositions and methods via the capture within the liposomes of free, unconjugated biotin present in the biochemical assay.

In some embodiments, the liposome is permeable to substances having a molecular weight of less than about 600 Da, and impermeable to substances having a molecular weight of about 600 Da or greater. That is, substances having a molecular weight of less than about 600 Da are allowed to pass by diffusion through the pores in the membrane of the liposome. The diffusion can be passive diffusion. The diffusion can be driven by osmosis, for example, whereby the interferents travel a concentration gradient from a high concentration outside of the liposomes to a low concentration inside the liposomes.

In some embodiments, the liposome is about 100 nanometers to about 1000 nanometers in diameter. In some embodiments, the liposome can be about 100 nanometers, about 200 nanometers, about 300 nanometers, about 400 nanometers, about 500 nanometers, about 600 nanometers, about 700 nanometers, about 800 nanometers, about 900 nanometers, or about 1000 nanometers in diameter. A population of the liposomes described herein can have a distribution of diameters represented by a mean diameter for the population. The mean diameter can be about 100 nanometers, about 200 nanometers, about 300 nanometers, about 400 nanometers, about 500 nanometers, about 600 nanometers, about 700 nanometers, about 800 nanometers, about 900 nanometers, or about 1000 nanometers. A population of liposomes can have a bimodal or multimodal distribution of diameters, according to some embodiments.

Suitable liposomes for use in the compositions described in this application include multilamellar vesicles (MLVs), small unilamellar liposome vesicles (SUVs), large unilamellar liposome vesicles (LUVs), and giant unilamellar liposome vesicles (GUVs). In some embodiments, the lipid bilayer can comprise sphingolipids, glycerophospholipids, sterols, and sterol derivatives. Sphingolipids to be used can include sphingomyelin and ceramides containing saturated, monounsaturated, and/or polyunsaturated acyl chains of different lengths. Phospholipids with various headgroup structures can be used, including phosphatidic acid (PA), phosphatidylcholine (PC), phosphatidylethanolamine (PE), phosphatidylglycerol (PG), phosphatidylinositol (PI), cardiolipin, phosphatidylserine (PS) containing saturated, monounsaturated, and/or polyunsaturated acyl chains of different lengths. Sterols and sterol derivatives to be used can include cholesterol, brassicasterol, allocholesterol, cholesterol methyl ether, campestanol, campesterol, cholesteryl acetate, coprostanol, desmosterol, dehydrodesmosterol, dihydrocholesterol, dihydrolanosterol, epicholesterol, lathosterol, lanosterol, sitostanol, sitosterol, stigmasterol, zymostenol, and zymosterol.

Lipids that can be used to form the porous liposomes can comprise either natural or synthetic sphingolipids, glycerophospholipids, sterols, and sterol derivatives. Sphingolipids can be used include sphingomyelin and ceramides containing saturated, monounsaturated, and/or polyunsaturated acyl chains of different lengths. Phospholipids with various headgroup structures can be used include phosphatidic acid (PA), phosphatidylcholine (PC), phosphatidylethanolamine (PE), phosphatidylglycerol (PG), phosphatidylinositol (PI), cardiolipin, phosphatidylserine (PS) containing saturated, monounsaturated, and/or polyunsaturated acyl chains of different lengths. Sterols and sterol derivatives can be used include but not limited to cholesterol, brassicasterol, allocholesterol, cholesterol methyl ether, campestanol, campesterol, cholesteryl acetate, coprostanol, desmosterol, dehydrodesmosterol, dihydrocholesterol, dihydrolanosterol, epicholesterol, lathosterol, lanosterol, sitostanol, sitosterol, stigmasterol, zymostenol, and zymosterol.

Mixtures of lipids can also be used, including mixtures of sphingolipids, glycerophospholipids, sterols, and sterol derivatives. Sterols and sterol derivatives should not be used alone, i.e. sterols and sterol derivatives should be included in mixtures having sphingolipid- or glycerophospholipid-containing liposomes in a range of from about 0% to about 40% of total lipids.

Preferred sphingolipids can comprise porcine brain sphingomyelin, chicken egg sphingomyelin, and bovine milk sphingomyelin. Preferred glycerophospholipids can comprise phospholipids with various headgroup structures such as phosphatidylcholine (PC), phosphatidylethanolamine (PE), phosphatidylglycerol (PG), phosphatidylinositol (PI), cardiolipin, phosphatidylserine (PS) with two saturated acyl chains of different lengths (e.g., 1,2-dipalmitoyl-sn-glycero-3-phosphocholine, 1,2-distearoyl-sn-glycero-3-phosphocholine, 1,2-dipalmitoyl-sn-glycero-3-phosphoethanolamine, 1,2-distearoyl-sn-glycero-3- phosphoethanolamine, 1,2-dipalmitoyl-sn-glycero-3-phospho-(1'-rac-glycerol), 1,2-distearoyl-sn-glycero-3-phospho-(1'-rac-glycerol), 1,2-dipalmitoyl-sn-glycero-3-phospho-(1'-myo-inositol), 1,2-distearoyl-sn-glycero-3-phosphoinositol, 1',3'-bis[1,2-dipalmitoyl-sn-glycero-3-phospho]-glycerol, 1',3'-bis[1,2-distearoyl-sn-glycero-3-phospho]-glycerol, 1,2-dipalmitoyl-sn-glycero-3-phospho-L-serine, 1,2-distearoyl-sn-glycero-3-phospho-L-serine), and with one saturated acyl chain of different lengths and one monounsaturated acyl chain of different lengths (e.g., 1-palmitoyl-2-oleoyl-sn-glycero-3-phosphocholine, 1-stearoyl-2-oleoyl-sn-glycero-3-phosphocholine, 1-palmitoyl-2-oleoyl-sn-glycero-3-phosphoethanolamine, 1-stearoyl-2-oleoyl-sn-glycero-3-phosphoethanolamine, 1-palmitoyl-2-oleoyl-sn-glycero-3-phospho-(1'-rac-glycerol), 1-stearoyl-2-oleoyl-sn-glycero-3-phospho-(1'-rac-glycerol), 1-palmitoyl-2-oleoyl-sn-glycero-3-phosphoinositol, 1',3'-bis[1-palmitoyl-2-oleoyl-sn-glycero-3-phospho]-glycerol, 1-palmitoyl-2-oleoyl-sn-glycero-3-phospho-L-serine, 1-stearoyl-2-oleoyl-sn-glycero-3-phospho-L-serine), and with one saturated acyl chain of different lengths and one polyunsaturated acyl chain of different lengths (e.g., 1-palmitoyl-2-linoleoyl-sn-glycero-3-phosphocholine, 1-stearoyl-2-linoleoyl-sn-glycero-3-phosphocholine, 1-palmitoyl-2-linoleoyl-sn-glycero-3-phosphoethanolamine, 1-stearoyl-2-linoleoyl-sn-glycero-3-phosphoethanolamine, 1-palmitoyl-2-linoleoyl-sn-glycero-3-phospho-(1'-rac-glycerol), 1-stearoyl-2-linoleoyl-sn-glycero-3-phospho-(1'-rac-glycerol), 1-palmitoyl-2-linoleoyl-sn-glycero-3-phospho-L-serine, 1-stearoyl-2-linoleoyl-sn-glycero-3-phospho-L-serine). Preferably, each fatty acid acyl chain has a number of carbon atoms ranging from about 16 to 20, most preferably 16, 18, or 20 carbon atoms. A preferred number of double bonds per each fatty acid acyl chain ranges from 0 to 2. Preferred sterols and sterol derivatives for use with sphingolipid- or glycerophospholipid-containing liposomes can comprise cholesterol, dihydrocholesterol, epicholesterol, sitosterol, and lathosterol. Cholesterol is the most preferred sterol. Preferred sphingolipids and glycerophospholipids can be used either alone or as a mixture of sphingolipids and glycerophospholipids in the presence of preferred sterols and sterol derivatives to form the porous liposomes described in this application. For example, in preferred embodiments, the liposomes can comprise 100% porcine brain sphingomyelin or a mixture of porcine brain sphingomyelin and cholesterol. Preferably, sterols and sterol derivatives can be in the range of from about 20% to about 40% of total lipids, most preferably about 30%.

The porous liposomes can comprise modified phospholipids. For example, sphingolipids and glycerophospholipids can be modified with small molecules, polyethylene glycol (PEG), fluorescent molecules, fluorescent PEG, and/or bromine. It is to be appreciated that the lipids can be modified with other materials not defined herein.

Sphingolipids and glycerophospholipids, sterols, sterol derivatives, and modified versions of lipids are readily available commercially from various sources, such as Sigma-Aldrich (St. Louis, MO); Invitrogen (Carlsbad, CA); Avanti Polar Lipids (Alabaster, AL); Fisher Scientific (Pittsburgh, PA); Steraloids (Newport, RI).

In some embodiments, the compositions described herein are provided in the form of a suspension. The suspension can comprise a buffer, for example phosphate buffer, e.g., phosphate buffered saline. The suspension can include pH-stabilizing or pH-adjusting agents, including, for example, sodium hydroxide and/or hydrochloric acid. In some embodiments, the suspension can have a pH-value of about 7.4 or can be adjusted to about 7.4 using pH-adjusting agents. Suitable pH-ranges for suspensions according to some embodiments include a pH-value of about 7.2 to about 7.6 or about 7.2, about 7.3, about 7.4, about 7.5, or about 7.6.

In some embodiments, the compositions described herein are provided in a "dry form," or in a form not suspended in liquid medium. The "dry form" of the compositions can include dry powders, lyophilized compositions, spray-dried, or precipitated compositions. The "dry form" compositions can include one or more lyoprotectants, such as sugars and their corresponding sugar alcohols, such as sucrose, lactose, trehalose, dextran, erythritol, arabitol, xylitol, sorbitol, and mannitol; amino acids, such as arginine or histidine; lyotropic salts, such as magnesium sulfate; polyols, such as propylene glycol, glycerol, poly(ethylene glycol), or poly(propylene glycol); and combinations thereof. Additional exemplary lyoprotectants include gelatin, dextrins, modified starch, and carboxymethyl cellulose. Preferred sugar alcohols are those compounds obtained by reduction of mono- and di-saccharides, such as lactose, trehalose, maltose, lactulose, and maltulose. Additional examples of sugar alcohols are glucitol, maltitol, lactitol and isomaltulose. The compositions/suspensions can be reconstituted from the above-described "dry-form" composition by dissolving them in a suitable diluent. The diluent can contain buffers, preservatives, or other appropriate excipients or additives.

This patent application also describes methods of preparing a biological sample for analysis comprising incubating the biological sample with the compositions as described herein. In this way, interferents present in the biological sample can be captured and sequestered within the porous liposomes prior to performing a biological analysis. The biological analysis can be an immunoassay, a clinical chemistry assay, or other clinical or diagnostic tests. The biological sample can be, for example, whole blood, serum, plasma, urine, saliva, semen, or cerebrospinal fluid. In some embodiments, the porous liposomal compositions can be added to or incubated with other reagents for the biochemical assay, not the biological sample. For example, the porous liposomal compositions can be incubated with a buffer provided as a component of a biochemical assay. Additionally, the porous liposomal compositions can be incubated with a reaction mixture for a biochemical assay which mixture includes one or more reagents for the assay and the biological sample. In some embodiments, the porous liposomal compositions are added in suspension form to the biological sample, the reagent, or the reaction mixture for a biochemical assay. In some embodiments, the porous liposomal compositions are reconstituted from "dry form" in the biological sample, the reagent, or the reaction mixture or in one or more components that contribute to the reaction mixture for the biochemical assay.

Incubating the biological sample, the reagent, and/or the reaction mixture or one or more components of the reaction mixture with the porous liposomal compositions described herein can result in the liposomes capturing one or more interferents from the biological sample, the reagent, and/or the reaction mixture. By diffusion, including passive diffusion, the one or more interferents pass through the pores of the liposomes. Each interferent can have a maximum cross-section that is less than the inner diameter of the pores; alternatively or additionally, each interferent can have a molecular weight that is less than the exclusion limit of the pores. In some embodiments, interferents can have a molecular weight of less than about 600 Da, and the pores can have a size exclusion limit of less than 600 Da so that only substances or molecules less than 600 Da can diffuse through. As described above, the one or more interferents can comprise, for example, biotin, fluorescein, bilirubin, or combinations thereof, and they can be unconjugated.

The liposomes described in this application can be provided as isolated liposomes substantially free of impurities. Impurities in a liposome preparation can include lipid aggregates, lipids not incorporated into (i.e., external to) liposomes, protein aggregates, and proteins not incorporated into (i.e., external to) liposomes. Moreover, the liposomes can be isolated after use, i.e., after incubation with a biological sample in a biochemical assay. Thus, this application includes methods of isolating liposomes either before or after use in a biochemical application or assay. Isolating the liposomes can comprise using centrifugation, dialysis, filtration, chromatography, magnetic separation, hollow fiber dialysis, or combinations thereof. The methods can further comprise separating or extracting the liposomes from the biological sample. That is, the methods of isolating can also be used to separate or extract the liposomes from the biological sample or reaction mixture. Separating or extracting the liposomes in this manner can include removing from the biological sample or reaction mixture any interferents captured within the liposomes. Thus, by isolating and separating or extracting the liposomes, interferents can be eliminated from a biological sample, a reagent for use in a biochemical assay, or a reaction mixture or one or more components of a reaction mixture for use in a biochemical assay. In this manner, the compositions described herein can also be used in methods of reducing or eliminating one or more interferents present in an assay of a biological sample.

However, it will be appreciated that the porous liposomes as described herein can remain in the biological sample and/or the reaction mixture, and the assay can be carried out without a washing or separation step. The porous liposomes reduce the concentration of interferents in the reaction, for example, by providing a semipermeable membrane that separates substances in solution by the difference in their diffusion rate through the porous liposome membrane, reducing the concentration of the interferents relative to the components of the reaction of the assay.

Also described herein are methods of making liposomes for use in the compositions described in this patent application. Suitable liposomes for use in the compositions described in this application include multilamellar vesicles (MLVs), small unilamellar liposome vesicles (SUVs), large unilamellar liposome vesicles (LUVs), and giant unilamellar liposome vesicles (GUVs). Preferred lipid compositions include sphingomyelin and glycerophospholipids such as PC, PE, PG, and PS with two saturated acyl chains, or one saturated and one monounsaturated acyl chain. Preferred numbers of carbon atoms per each fatty acid acyl chain for PC, PE, PG and PS include 16, 18, or 20 carbon atoms. Preferred numbers of double bonds per each fatty acid acyl chain ranges from 0 to 2. Cholesterol is the most preferred sterol. Preferred ratios of lipids in liposomes include natural sphingomyelin or glycerophospholipids with two saturated acyl chains comprising about 40% of the total lipids, and glycerophospholipids with one saturated and one monounsaturated acyl chain comprising about 30% of the total lipids, and cholesterol comprising about 30% of the total lipids. For example, in a preferred embodiment, the lipid composition of a porous liposome according to the present application can be 40% porcine brain sphingomyelin, 30% 1-palmitoyl-2-oleoyl-sn-glycero-3-phosphocholine, and 30% cholesterol, expressed as percentages of the total lipids. An example of a binder that can be disposed within the liposomes is avidin. In one embodiment, large unilamellar vesicles (LUVs) with mean diameter 200 nm and with avidin binder disposed within the liposomes can be prepared by dispersing dried lipid films and extruding them through polycarbonate filters in, for example, 5 mg/mL avidin containing 20 mM PBS, pH 7.4 buffer. A sepharose CL4B column can be used to remove excess avidin residing in the exterior of the liposome preparation, thereby generating liposomes with avidin only in the interior of liposomes. Dynamic light scattering (DLS) measurements can be conducted both before and after sepharose CL4B column purification to determine the size of the formed liposomes. In some embodiments, the particle-size distribution of the liposomes represents a mean diameter of 200 nm for the liposomes before and after purification.

Also described herein are kits comprising porous liposomal compositions along with one or more reagents for performing a biochemical assay on a biological sample and instructions for performing the biochemical assay. The kits can be prepared for use in a biochemical assay including, for example, an immunoassay or a clinical chemistry assay or other medical or diagnostic test. The instructions can further direct a user to incubate the biological sample or other kit component with the compositions described herein. In some embodiments, the kits comprise the lyophilized compositions described herein along with one or more reagents for performing a biochemical assay on a biological sample and instructions for performing the biochemical assay. The instructions can further direct a user to reconstitute the lyophilized composition and incubate the biological sample or other kit component with the reconstituted composition. Alternatively, the instructions can direct a user to reconstitute the lyophilized composition in the biological sample or other kit component without a prior reconstitution step. That is, the kits' reagents can include as aspects of one or more reagents appropriate diluents for reconstituting "dry form" porous liposomal compositions according to the present application. The kits disclosed herein can include packaging, labeling, safety information, and any other written material that would be helpful to a user in performing a diagnostic assay including use of the porous liposomal compositions.

Figure 1:
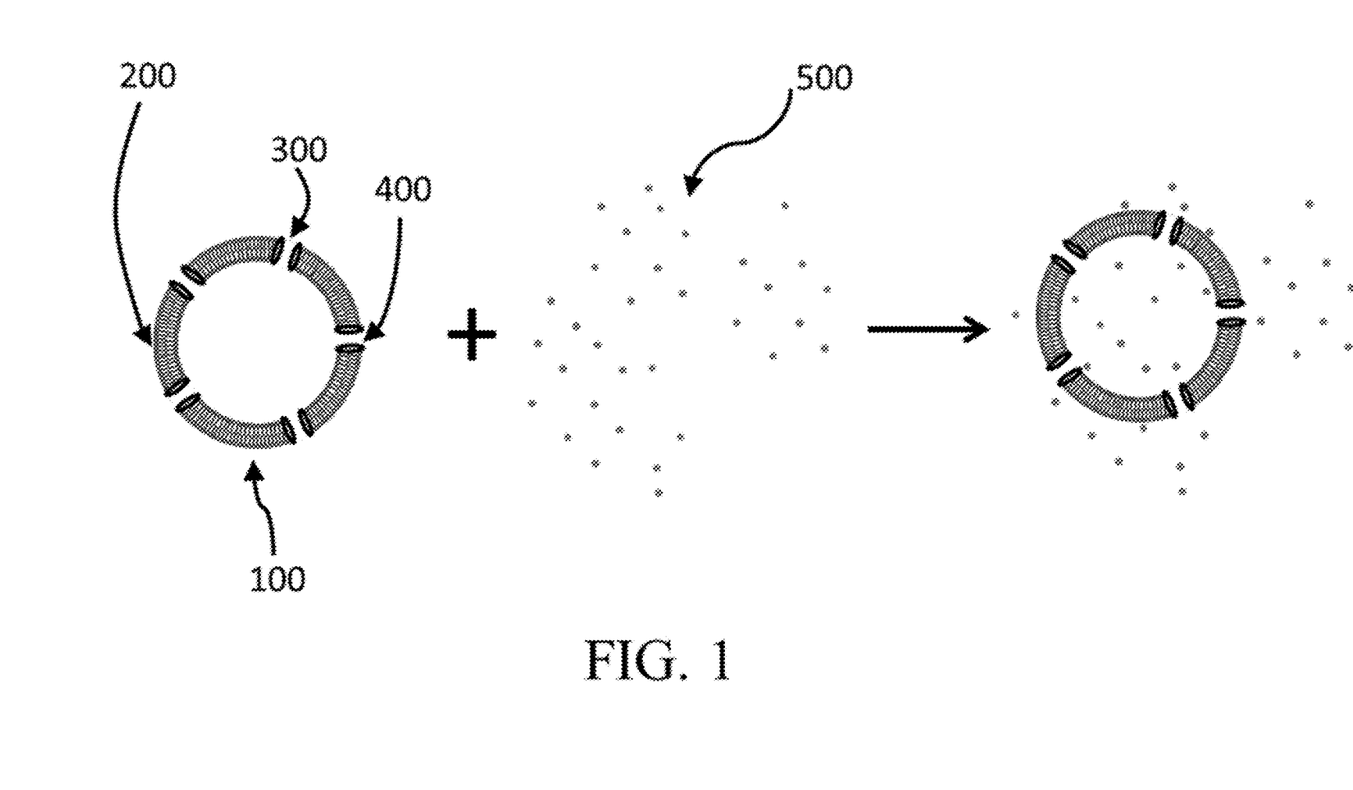
FIG. 1 is an exemplary depiction of porous liposomes absorbing interfering substances according to one embodiment of the subject matter described herein.

Particular embodiments of the compositions and methods disclosed herein are schematically represented in the appended figures. The representations in the figures are examples only, and do not limit the scope of the compositions and methods described in this application. The figures depict compositions and methods for removing interfering substances from, for example, biological samples using porous liposomes. For example, as schematically represented in FIG. 1, a liposome 100 can comprise a lipid bilayer 200. A pore 300 is formed in the lipid bilayer by the presence of pore-forming substance 400, yielding a porous liposome capable of removing interfering substance 500 from, for example, a biological sample or a biochemical assay reaction by capturing the interfering substance inside the liposome. The porous liposomes reduce the concentration of interferents in the sample and/or the reaction mixture. Substances are separated in solution by the difference in their diffusion rate through the porous liposome membrane, reducing the concentration of the interferents relative to the components of the reaction of the assay. The porous liposomes may remain in the sample and/or the reaction mixture even when homogeneous assays are used that do not include a washing or separation step.

Figure 2A:
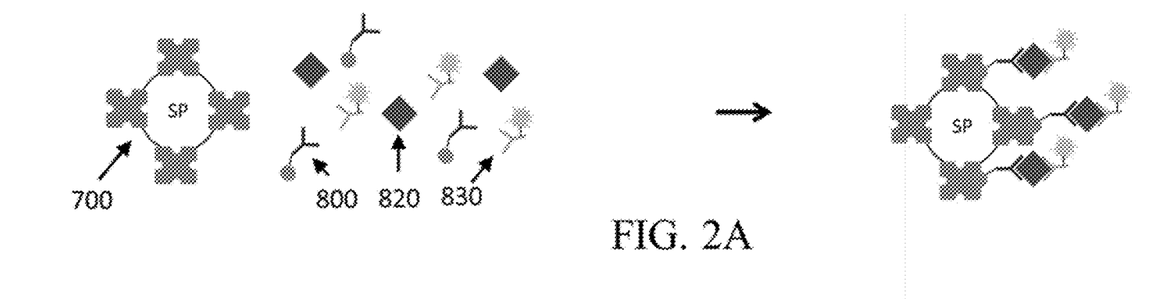
FIG. 2A shows an example reaction without interfering substances.
Figure 2B:
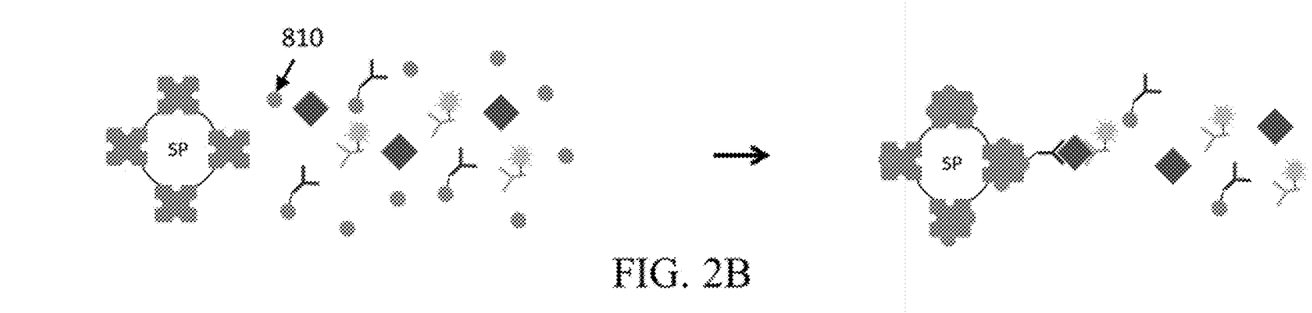
FIG. 2B shows interfering substances interfering with a reaction according to that shown in FIG. 2A, wherein the formation of immune complexes is hampered, giving a falsely low measurement of analyte concentration.
Figure 2C:
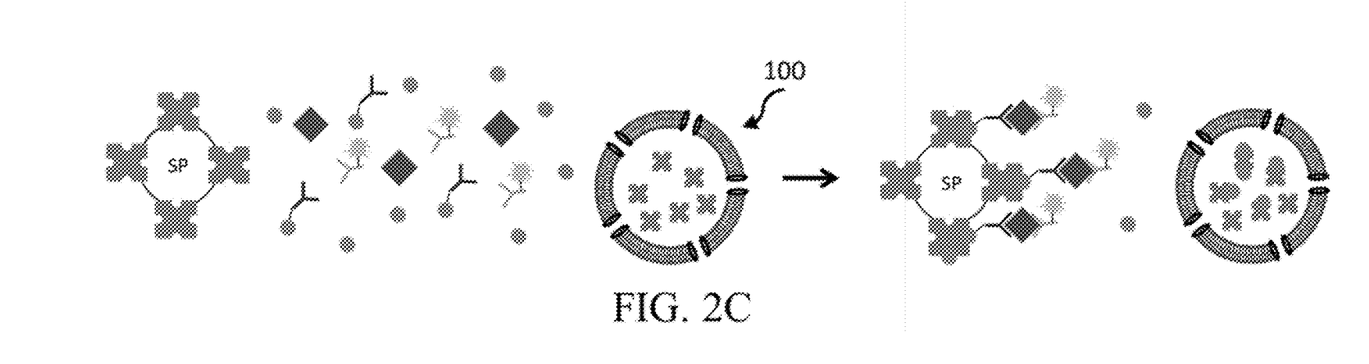
FIG. 2C shows mitigation of the interference depicted in FIG. 2B by the presence of porous liposomes according to an embodiment of the subject matter described herein.

In some embodiments, the portion of the interfering substance 500 captured inside the liposome cannot interfere with the reaction of the biochemical assay, as schematically represented in FIGS. 2A-2C. In the absence of interfering substance (FIG. 2A), a primary probe, which can comprise a conjugated interferent 800, is free to bind to a solid support particle (SP) 700 and a target analyte 820. The primary probe, which can be a conjugated interferent 800 can be conjugated to a molecule (e.g., biotin) that specifically binds a binding site of the solid support particle (e.g., avidin). A secondary probe 830 also binds the target analyte 820, and a complex comprising the solid support, the primary and secondary probes, and the target analyte is formed without interference or with reduced interference. The presence of unconjugated interferent (e.g., free biotin) 810, however (FIG. 2B), can, in one example, act as an interferent and occupy binding sites (e.g., avidin) on the solid support particle and thereby reduce formation of the probe/analyte/solid support complex, reducing the efficiency of the biochemical assay. Introducing porous liposome 100 comprising binder 600 (e.g., avidin) into the reaction (FIG. 2C) can capture unconjugated interferents (e.g., free biotin) inside the liposome, and thereby sequester them from the reaction, allowing the complex comprising the solid support, the primary and secondary probes, and the target analyte to form.

Figure 3:
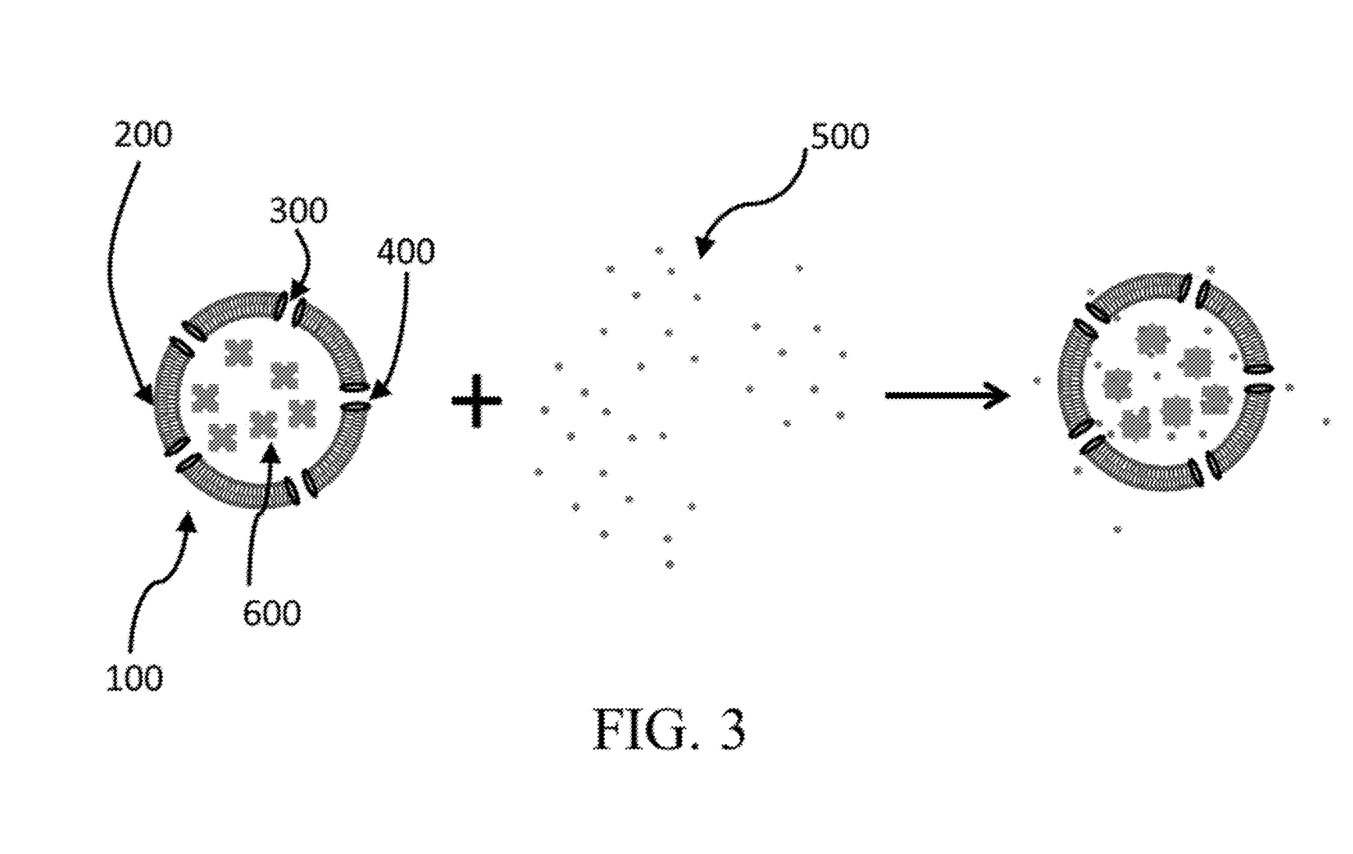
FIG. 3 is an exemplary depiction of porous liposomes containing binders in accordance with an embodiment of the subject matter described herein.
Figure 4:
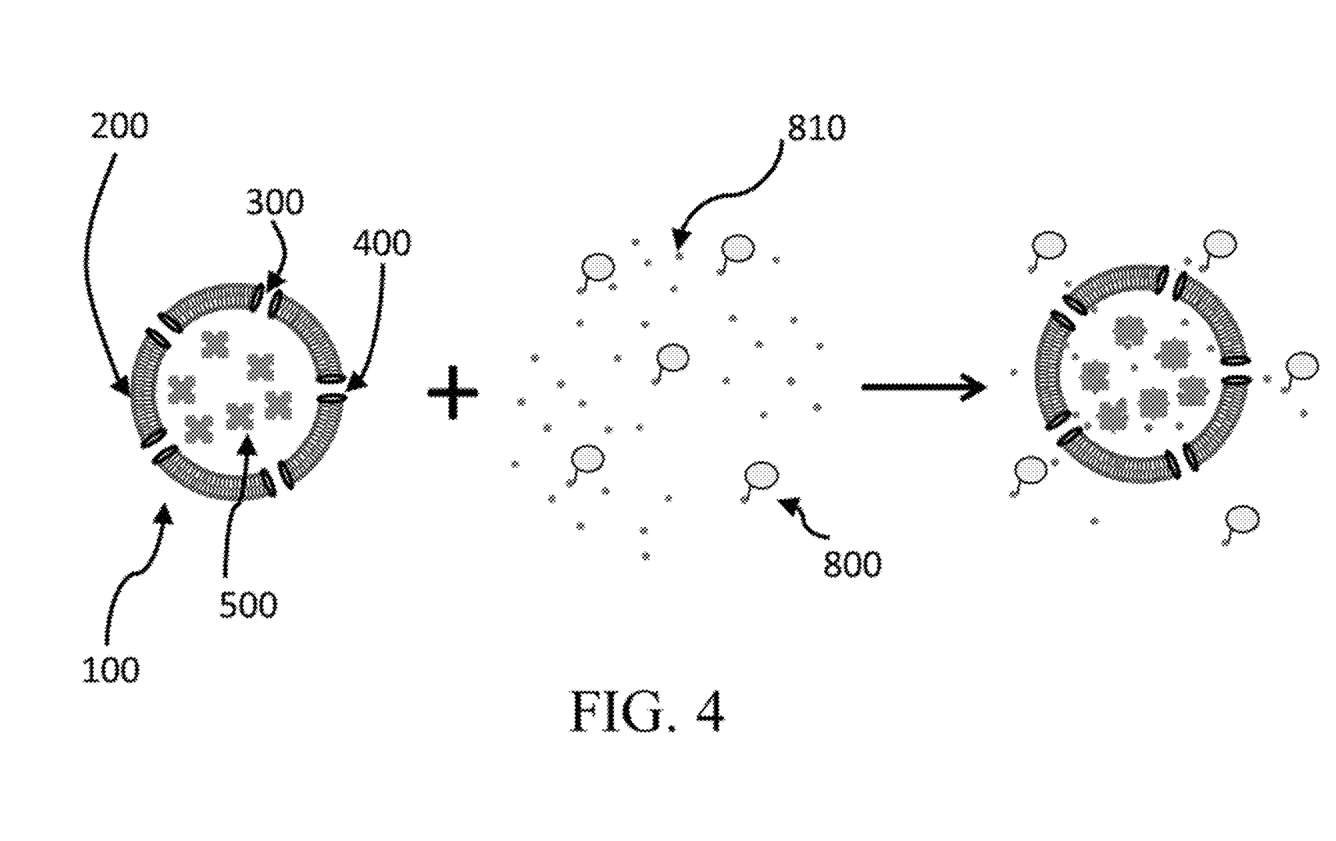
FIG. 4 is an exemplary depiction of porous liposomes containing binders in accordance with an embodiment of the subject matter described in this patent application, wherein conjugates that contain the interfering substances and that have a minimum cross-section greater than the inner diameter of the pores or molecular weight greater than the size exclusion limit of the pores do not enter the liposome and are available in the reaction mixture of a biochemical assay.

As schematically represented in FIG. 3, the porous liposome 100 can, in some embodiments, contain a binder 600 that binds the interfering substance 500, leading to enrichment of the interfering substance within the liposome and further reducing the concentration of interfering substance in the biochemical assay reaction volume. In some embodiments, the interfering substance is introduced into the biochemical assay as a component of the assay itself (FIG. 4). For example, conjugated interferent 800 (in some examples, biotin or fluorescein conjugated to a probe) can be used in an assay. In these cases, the interference by the interfering substance can be particularly pronounced, as unconjugated interferent 810 (i.e., free biotin or free fluorescein) will interfere with the remaining assay components. In some embodiments, the pore size of the porous liposome only allows for the unconjugated interfering substances to enter the liposome, thereby reducing interference by the unconjugated interfering substances in the assay. In the case of biotin and fluorescein interfering substances, binders may be avidin or its derivatives and anti-fluorescein antibodies, respectively. The pores in the liposomes can be introduced by pore-forming proteins including, for example, porins, hemolysin, and nucleoporin. Other pore-forming proteins suitable for use in the compositions and methods described herein include, without limitation, monomers, multimers, and combinations of porin, hemolysin, and nucleoporin. In addition, protein complexes including, for example, the membrane attack complex (MAC) of the complement system, component C9 of the complement system, or subunits, combinations, and multimers of MAC or component C9 can be used as pore-forming substances. The pore-forming substances can be recombinant pore-forming proteins, chimeric pore-forming proteins, genetically engineered pore-forming proteins, and pore-forming proteins conjugated to other molecules of interest. Other molecules of interest can include, for example, epitopes, antigens, or other binding molecules useful for: molecularly or immunogenically labelling or purifying the pore-forming substances or liposomes comprising them; or isolating the pore-forming substances or liposomes comprising them. For example, in some embodiments, the pore-forming substance can be conjugated to a 6-his tag (6-histidine), a Myc tag, an HA tag, FLAG tag, or similar epitope tag to facilitate separation or isolation of the liposomes from a mixture comprising the compositions described herein and, for example, a biological sample. In addition to the use of pore-forming proteins, porous phospholipid nanoshells ("PPNs") can be employed, as described above. In some embodiments, the pore size defines the size or molecular weight of the interfering substances that may be captured in the porous liposomes and thereby sequestered from or removed from the reaction volume of the biochemical assay. Taking the example of biotin interference, the porous liposomes can use porins that only allow diffusion of compounds below 600 g/mol. Porous liposomes having porin-formed pores are permeable to free biotin (molecular weight (Mr)=244.3 g/mol) through free, passive diffusion, but are impermeable to, for example, a biotin-antibody conjugate, which in some embodiments has a molecular weight of greater than 600 g/mol, or about 150,000 g/mol.

EXAMPLES

The following examples are provided to further describe some of the embodiments disclosed herein. The examples are intended to illustrate, not to limit, the disclosed embodiments.

Example 1: Measurement of Porin Topography by FRET (Forster/Fluorescence Resonance Energy Transfer)

To determine the insertion of porin in the lipid bilayer of liposomes, FRET experiments were performed using Tryptophan (Trp) residues of porin as FRET donor and pyrene-PC [1-hexadecanoyl-2-(1-pyrenedecanoyl)-sn-glycero-3-phosphatidylcholine] residing in the lipid bilayer as FRET acceptor. 200 micromolar small unilamellar vesicles (SUVs) containing 20 μg/mL porin were prepared in the presence (F samples) and absence (Fo samples) of 5 mol % pyrene-PC. FRET measures the distances between the donor and acceptor and therefore provides information about the membrane insertion of porin. If the distance between two FRET pairs is in close proximity, the energy of the absorbed light can be transferred directly from the donor to the acceptor. The consequence of FRET is the decrease in the fluorescence intensity of the donor (Trp) in the presence of acceptor (pyrene-PC) as compared to the fluorescence intensity of the donor in samples lacking the acceptor. The reduction of fluorescence intensity in the presence of pyrene-PC (Table 1) shows that porins are inserted in the lipid bilayer of SUVs.

Example 2: Preparation, Purification, and Stability Assessment of Liposomes Encapsulating Avidin Avidin trapped large unilamellar vesicles (LUVs) with mean diameter 200 nm were prepared by dispersing dried lipid films and extruding them through polycarbonate filters in 5 mg/mL avidin containing 20 mM PBS, pH 7.4 buffer. A sepharose CL4B column was used to remove avidins residing in the exterior of the liposomes, thus generating liposomes with avidin only in the interior of liposomes. Dynamic light scattering (DLS) measurements were conducted both before and after Sepharose CL4B column purification. The particle-size distribution of the liposomes obtained showed that the mean diameter of the liposomes was still maintained approximately at 200 nm after the purification step (data not included).

In proteins, the indole group of tryptophan (Trp) is considered the dominant intrinsic fluorophore. The binding of biotin to avidin was assessed by measuring Trp fluorescence emission intensity. Tryptophan residues in avidin have a peak absorbance near 280 nm, and the maximum emission intensity ($\lambda$max) ranges from 308 to 355 nm, depending on solvent polarity. The $\lambda$max is blue-shifted (shift to shorter wavelength) if the Trp is in a hydrophobic environment and is red-shifted (shift to longer wavelength) when the Trp is exposed to an aqueous environment. Avidin has four high affinity binding sites for biotin, and the binding of biotin to avidin changes the environment of tryptophan residues in avidin, causing blue shifts in the emission peak from 337 to 328 nm. Purified avidin-trapped liposomes have $\lambda$max around 338 nm. No change in $\lambda$max was observed for up to 4 hours of incubation with externally added biotin (10 µg/ml), indicating that no leakage or release of avidin occurred in purified LUVs. To test the availability of externally added biotin in this sample, more avidins (0.1 mg/mL) were added into externally-added-biotin containing avidin-trapped LUVs and allowed to interact with previously externally added biotin for 5 minutes, displaying a blue-shifted $\lambda$max from 337±0.4 to 328±0.6 nm (Table 2).

Example 3: Influx of Biotin Via Pores Formed by Porin in the Lipid Bilayer of Avidin-Trapped Liposomes The influx of biotin through the porin-induced pores in the lipid bilayer of avidin-trapped liposomes was measured by observing blue shifted Trp emission fluorescence of avidins. LUVs were prepared by dispersing and extruding the lipid films, as described above, in the presence of 1 mg/mL avidin and 50 µg/mL porin. Porin-embedded liposomes with captured avidin were purified by a sepharose CL4B column to remove external avidin.

For protein emission spectra, purified porin-embedded liposomes with trapped avidin were excited at 280 nm and emission was acquired from 300-370 nm. The spectra were monitored before and after external addition of biotin to the liposome containing solution. Purified avidin-trapped, porin-embedded liposomes have $\lambda$max around 338±0.5 nm in the absence of externally added biotin. As shown in Table 3, the Trp $\lambda$max shifts from 338±0.5 to 334±1.3 nm as externally added biotin is transported into the liposomes through the pores followed by binding of biotin to liposomal avidin. It should be noted that the Trp emission fluorescence is not only from avidin but also from porin, which exhibits biotin interaction independent Trp emission spectra.

TABLE 1

Quenching of Trp fluorescence by pyrene

| | Fo (without 5 mol % FRET acceptor) | F (with 5 mol % FRET acceptor) |
|---|---|---|
| Fluorescence Intensity at 335 nm (% FRET = 30.9 ± 1.3%) | 520.4 ± 7.4 | 359.6 ± 1.8 |

Average (mean) values and S.D. from 20 replicates are shown. Trp emission intensity was measured with an excitation wavelength at 280 nm and an emission wavelength at 355 nm. F/Fo, the fraction of fluorescence that is unquenched due to FRET, was then calculated as [% FRET = (1 − F/Fo) × 100%].

TABLE 2

The shift in $\lambda$max upon binding of biotin to avidin

| | Purified avidin-trapped LUVs | Purified avidin-trapped LUVs + Externally added biotin (4 hours incubation) | Purified avidin-trapped LUVs + Externally added biotin + Externally added avidin (5 minutes incubation) |
|---|---|---|---|
| $\lambda$max (nm) | 338 ± 0.8 | 337 ± 0.4 | 328 ± 0.6 |

Average (mean) values and S.D. from 4 replicates are shown. For Trp fluorescence emission spectra, samples were excited at 280 nm, and emission was acquired from 300-370 nm. Purified avidin-trapped LUVs were incubated with externally added biotin for 4 hours, and then 0.1 mg/ml of avidin was externally added and incubated for 5 minutes to determine the availability of externally added biotin.

TABLE 3

The shift in $\lambda$max upon transport of biotin into liposomes

| | Purified avidin-trapped, porin-embedded LUVs | Purified avidin-trapped, porin-embedded LUVs + Externally added biotin |
|---|---|---|
| (nm) | 338 ± 0.5 (3) | 334 ± 1.3 (11) |

The number of samples is shown in parentheses. For Trp fluorescence emission spectra, samples were excited at 280 nm, and emission was acquired from 300-370 nm. Biotin was added externally to purified liposomes at a concentration of 10 µg/ml and incubated for 2 hours.

What is claimed is:

1. A composition comprising a liposome, the liposome comprising an interior, a binder disposed to the interior of the liposome, and a lipid bilayer comprising pores formed by a pore-forming substance in the lipid bilayer, wherein the binder has binding specificity for one or more interferents.

2. The composition of claim 1, wherein the pore-forming substance forms pores in the lipid bilayer.

3. The composition of claim 1, wherein the pore-forming substance comprises a pore-forming protein or protein complex comprising porin, hemolysin, nucleoporin, membrane attack complex of the complement system, complement C9 multimer, or combinations thereof.

4. The composition of claim 1, comprising about 1 µg/ml to about 100 µg/ml of the pore-forming substance.

5. The composition of claim 2, wherein the pores allow passage of one or more interferents into the liposome via diffusion.

6. The composition of claim 2, wherein the pores have an inner diameter of about 0.5 nanometers to about 12 nanometers or an exclusion limit of about 250 Da to about 5000 Da.

7. The composition of claim 1, wherein the binder has a maximum cross-section that is greater than the inner diameter of the pores or the binder is larger than the exclusion limit of the pores.

8. The composition of claim 7, wherein at least a portion of the binder is disposed in the lipid bilayer.

9. The composition of claim 7, wherein the binder is disposed entirely within the interior of the liposome.

10. The composition of claim 1, wherein the binder comprises one or more binding sites, each binding site having an affinity for one or more interferents.

11. The composition of claim 1, wherein the binder comprises avidin, streptavidin, or neutravidin.

12. The composition of claim 1, wherein the binder is an antibody, an aptamer, an affibody, an affimer, a fragment of an antibody, a fragment of an aptamer, a fragment of an affibody, or a fragment of an affimer.

13. The composition of claim 10, wherein the affinity is an immunospecific affinity.

14. The composition of claim 1, wherein the liposome is permeable to substances having a molecular weight of less than about 600 Da, and impermeable to substances having a molecular weight of about 600 Da or greater.

15. The composition of claim 1, wherein the liposome is about 100 nanometers to about 1000 nanometers in diameter.

16. The composition of claim 1, wherein the liposome is about 200 nanometers in diameter.

17. The composition of claim 1, wherein the lipid bilayer comprises sphingolipids, glycerophospholipids, sterols, or sterol derivatives, or combinations of sphingolipids, glycerophospholipids, sterols, and sterol derivatives.

18. The composition of claim 1, wherein the composition is a suspension.

19. The composition of claim 18, further comprising a buffer.

20. The composition of claim 19, having a pH-value of about 7.4.

21. The composition of claim 1, wherein the composition is reconstituted from a lyophilized composition.

22. The composition of claim 1, wherein the composition is lyophilized.

23. A method of preparing a biological sample for analysis comprising incubating the biological sample with the composition according to claim 1.

24. The method of claim 23, wherein the analysis is an immunoassay, a clinical chemistry assay, or other clinical test.

25. The method of claim 23, wherein the biological sample is whole blood, serum, plasma, urine, saliva, semen, or cerebrospinal fluid.

26. The method of claim 23, wherein the incubating the biological sample with the composition captures within the liposomes one or more interferents from the biological sample.

27. The method of claim 26, wherein each interferent has a maximum cross-section that is less than the inner diameter of the pores or the one or more interferents each is less than about 5000 Da.

28. The method of claim 26, wherein the one or more interferents comprise biotin, fluorescein, bilirubin, or combinations thereof.

29. The method of claim 28, wherein the one or more interferents are unconjugated.

30. The method of any claim 27, wherein the one or more interferents each is less than about 600 Da.

31. The method of claim 23, further comprising isolating the liposomes.

32. The method of claim 31, wherein the isolating the liposomes comprises using centrifugation, dialysis, filtration, chromatography, magnetic separation, hollow fiber dialysis, or combinations thereof.

33. The method of claim 32, further comprising separating the liposomes from the biological sample.

34. A method of reducing or eliminating one or more interferents in an assay of a biological sample comprising incubating the biological sample with the composition of claim 1.

35. A kit comprising:
a. the composition claim 1;
b. one or more reagents for performing a biochemical assay on a biological sample; and
c. instructions for performing the biochemical assay, wherein the instructions further direct a user to incubate the biological sample with the composition.

36. A kit comprising:
a. the composition of claim 22;
b. one or more reagents for performing a biochemical assay on a biological sample; and
c. instructions for performing the biochemical assay, wherein the instructions direct a user to reconstitute the composition and incubate the biological sample with the reconstituted composition.

37. The composition of claim 4, comprising about 20 µg/ml of the pore-forming substance.

* * * * *